United States Patent [19]

Ogleby et al.

[11] Patent Number: 4,882,285
[45] Date of Patent: Nov. 21, 1989

[54] PROCESS FOR MONITORING THE QUANTITY OF DIMETHYL HYDANTOIN

[75] Inventors: John W. Ogleby; Neville J. Charkley, both of Warrington, United Kingdom

[73] Assignee: Laporte Industries Limited, London, England

[21] Appl. No.: 313,752

[22] Filed: Feb. 22, 1989

[30] Foreign Application Priority Data

Feb. 25, 1988 [GB] United Kingdom ................ 8804460

[51] Int. Cl.[4] ...................... G01N 31/22; G01N 33/00
[52] U.S. Cl. .......................... 436/98; 422/61; 422/55; 436/89; 436/163
[58] Field of Search ........................... 436/89, 98, 163; 422/55, 61

[56] References Cited

U.S. PATENT DOCUMENTS 4,119,535 10/1978 White et al. ...................... 210/755
4,698,165 10/1987 Theyson ............................. 210/755

Primary Examiner—Kenneth M. Schor
Assistant Examiner—Gregory Muir
Attorney, Agent, or Firm—Kane, Dalsimer, Sullivan, Kurucz, Levy, Eisele and Richard

[57] ABSTRACT

Pool or spa water can be monitored for dimethyl hydantoin content, as a residue of disinfection with halogenated hydantoin, by determining the quantity of base required to adjust the pH to 9.3. The pH may be judged by a suitable indicator for example thymol phthalein or thymol blue. The method can be applied either titrimetrically, or by comparison colorimetrically with standard solutions and may be modified for use in relation to other halogenated hydantoins. The method may be applied to the testing of pools for compliance with an advisory dimethyl hydantoin content limit and may be embodied in a kit for easy poolside use.

4 Claims, No Drawings

PROCESS FOR MONITORING THE QUANTITY OF DIMETHYL HYDANTOIN

This invention relates to a method of testing applicable to waters in swimming pools, or spa baths or the like where bodies of water are maintained for appreciable periods of time for human recreational or therapeutic use.

While a wide variety of materials may be used to achieve disinfection or germicidal action in pools halogenated hydantoin compounds, for example 1-bromo,3-chloro 5,5-dimethyl hydantoin, are in widespread use. These compounds hydrolyse and release their halogen content when dissolved in water leaving as a residue the parent hydantoin molecule, 5,5-dimethyl hydantoin.

It has been suggested that residues of halogenated hydantoins, particularly of dimethyl hydantoin, may be a contributory factor in causing bather skin irritation and/or skin rashes. A study by the United Kingdom Department of the Environment which was carried out in 1983–84 confirmed that Department's approval of bromochlorodimethyl hydantoin as a disinfectant for pool use subject to the maintainance of the concentration of residual dimethyl hydantoin in the water below 200 mg/l e.g. by appropriate water renewal. It was further recommended in the same study that the pH value of the water be between 7.4 and 7.8 in a correctly maintained pool or spa.

The requirement to monitor the concentration of hydantoin residues in water gives rise to problems in that there has hitherto been no simple pool-side means of doing this, the use of fairly sophisticated equipment and methods, such as high pressure liquid chromatography, being necessary.

The present invention provides a simple test which can be used to monitor the level of hydantoin residues in correctly maintained pools or other bodies of similar water. Such residues may be of any halogenated hydantoins whether the 1,3-di-chloro, dibromo, chlorobromo or other halo compounds and whether the 5,5-dimethyl compound, other dialkyl or diaryl comounds or alkaryl compounds.

According to the present invention water containing dimethyl hydantoin residues is basified to a pH of about 9.3 and the quantity of base required to achieve this used as a basis for determining the quantity of hydantoin present.

It has been discovered in the course of making the present invention that a proportion of the hydantoin residue, for example of dimethyl hydantoin, is still present at a water pH of about 7.4 to 7.8 as free acid and that the size of that proportion is sufficiently constant, at a given pH, to provide a basis for a test method. It has further been discovered that substantially all of the acidic dimethyl hydantoin residue is neutralised at a pH of about 9.3 and that the quantity of hydantoin residue may be determined by applying a non-stoichiometric factor which in the case of dimethyl hydantoin is $0.2 \times 10^{-4}$ equivalents of base = 3.33 mg dimethyl hydantoin. This factor compares with a theoretical equivalence of the same quantity of base to 2.56 mg dimethyl hydantoin.

If residues of hydantoins other than dimethyl hydantoin are required to be monitored according to this invention the pH at which all would be neutralised and the non-stoichiometric factor may vary slightly from the above but may be derived by test means. The principles of the present invention are not affected by such slight variance.

According to one aspect thereof the present invention provides a process for monitoring the quantity of dimethyl hydantoin in a water having a pH of about 7.4 to about 7.8 characterised by contacting a volume of base of known normality with a volume of the water and determining the quantity of dimethyl hydantoin therein according to the non-stoichiometric relationship $0.2 \times 10^{-4}$ equivalents of base = 3.33 mg of dimethyl hydantoin by a procedure selected from:

(a) adding a sufficient volume of the base to a given volume of the water or adding a sufficient volume of the water to a given volume of the base to attain a pH of 9.3 in the water so as to determine the actual quantity of dimethyl hydantoin in the water, (b) adding a volume of the base corresponding to a preselected concentration level of dimethyl hydantoin to a given volume of the water and determining the deviation of the pH of the water above or below 9.3 to determine the deviation of the concentration of dimethyl hydantoin respectively below or above that level in the water.

According to yet a further aspect thereof the present invention provides a kit for use for testing water for hydantoin residues according to the above process, the kit comprising a volume measure for the water to be tested, a supply of base having a given concentration, means for dispensing a volume of the base equivalent to a preselected quantity of dimethyl hydantoin in the volume of water taken or for dispensing and indicating the volume dispensed of a variable quantity of base, and means for indicating the pH of water. Depending on which of the previously described aspects of the present invention are to be operated, the means for dispensing a specific volume of base or of water may be of fixed volume, or may be capable of dispensing water or base progressively while indicating the volume dispensed, such as a calibrated pipette, syringe or other similar means.

While the present invention may be put into practice using a pH meter it is particularly suitable for the application of colorimetric means to determine the pH. Two indicator systems particularly suitable for use in the practice of the invention are thymol phthalein and thymol blue, the latter optionally containing a dye to enhance the colour indication for example, preferably, a yellow dye. One example of such a dye is Sandolan Yellow ETZ (Trade Mark).

Thymol phthalein develops a blue colour over the approximate pH range 9.3 to 10.5 and the initiation of the colour change is sufficiently marked to be used for the purposes of this invention. Preferably, to enhance the efficiency of this indicator a source of soluble iodine, such as sodium or potassium iodide, is also present.

Thymol blue develops a colour change from yellow to blue over the approximate pH range of 8 to 10. To enhance the efficiency of this indicator quantity of a water-soluble yellow dye which may for example be from 50% to 400% of the quantity of the thymol blue, may be added. This gives a yellow-green-blue colour change which is readily distinguished visually. This latter indicator is particularly suitable for use according to procedure (b) of the invention in that the colour change can be used to detect pH levels corresponding to reasonably small increments of dimethyl hydantoin concentration, for example increments of 50 mg/liter. Thus, standard solutions containing concentrations of dimethyl hydantoin differing by, for example, 50 mg/liter increments about a desired level or threshold and containing a standard quantity of base, which may be equivalent to the said threshold or level, and containing the thymol blue, or, preferably, the yellow dye-modified thymol blue indicator may be prepared to give a series of visually distinguishable colours. If a sample of water having the same volume and an unknown concentration of dimethyl hydantoin is tested by adding to it the indicator and the same standard quantity of base the concentration of dimethyl hydantoin therein can be determined by comparison with the standard solutions or with representations of the solutions such as colour photographs or a colour chart.

The accuracy of the methods of the present invention depend on the pH of the water being sampled as it is recognised that the pH will vary depending on the interval which has elapsed since the past pH adjustment. Preferably the pH of the water has been adjusted prior to the test to from 7.4 to 7.8, particularly preferably to 7.5+/−0.1. To be effective in monitoring hydantoin residues the test does not have to be extremely accurate particularly as it can be adjusted to indicate concentrations of neutralisable hydantoin somewhat below the 200 mg/l level. It is found that an accuracy of better than 50 mg/l and often better than 20 mg/l can be obtained.

There may be materials in the water which cause interference with the test results. For example, if the water had previously been disinfected using an isocyanurate, there could be a residue of cyanuric acid. Cyanuric acid competes with the hydantoin residues for reaction with base. If the water has had this history the content of cyanuric acid should be determined by means of separate tests, well known in the art, so that its presence may be allowed for in adjusting the test results.

A more frequent interfering factor is the presence in the water to be tested of the unhydrolysed halogenated hydantoin compound which would bleach an indicator such as thymol phthalein rendering it ineffective. To overcome this problem, the water is preferably treated with a soluble iodine source, even if a thymol phthalein indicator is not used, followed by a treatment with sodium thiosulphate or sulphite. The overall reactions of these compounds with unhydrolysed bromo-chlorodimethyl hydantoin (BCDMH) would be as follows:

$BCDMH + KI \rightarrow KCl + KBr + I_2 + DMH$

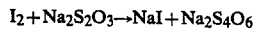

$I_2 + Na_2S_2O_3 \rightarrow NaI + Na_2S_4O_6$

The quantities of the above reactants or suitable equivalents therefor are preferably selected with regard to the requirements for such reactions.

In order to facilitate this pretreatment, a supply of a soluble iodide, or iodide solution, and of thiosulphate or sulphite or solution thereof is preferably included in the testing kit described above. The quantity of DMH generated by the above reactions is generally sufficiently small to be ignored in interpreting the overall test results.

The invention will now be illustrated by means of the following non-limiting examples and comparative tests. The Examples according to procedures (a) and (b) are according to the invention. Comparative figures obtained by high pressure liquid chromatography (HPLC) are also included.

Samples of water from a number of different spa pool installations which had used bromo-chloro-dimethyl hydantoin disinfection were obtained. Portions of these samples were analysed by HPLC to give a reference point for judging the accuracy of the methods of the present invention. The conditions used were

| | |
|---|---|
| Column | = Apex Octyldecyl 5μ |
| Flow rate | = 2 mls minute$^{-1}$ |
| Solvent | = Water |
| Detector Wavelength | = 230 nm |
| DMH retention time | = 8.8–8.9 minutes |

Other portions of the same samples were titrated to a pH of 9.3 using 0.02 Normal NaOH solution and thymol blue and the contents of dimethyl hydantoin calculated by applying the factor $0.2 \times 10^{-4}$ e.g. base = 3.33 mg dimethyl hydantoin. This corresponds to procedure (a) described above.

Other portions of the same samples were compared using an indicator with standard solutions according to procedure (b) described above.

The standard solutions and the indicator were prepared as follows.

Indicator

Dissolve 1 g Thymol Blue in 21.5 ml of 0.1N NaOH solution. Dilute to ca. 900 ml with demineralised water. Add a solution of 2 g Sandolan Yellow ETZ "225%" dye dissolved in 50 mls demineralised water. Dilute to 1 liter.

Preparation of Standard Solutions

Prepare 50, 100, 150, 200, 250 ppm solutions of dimethyl hydantoin in demineralised water. Take a 20 ml aliquot of each concentration in a clear glass vial. Adjust pH to 7.5 using 0.02N NaOH solution. Add 0.8 mls 0.02N NaOH solution, then 5 drops of indicator (using same dropping pipette throughout). Shake thoroughly.

Preparation of Sample for Comparison with Standard Colours

To 20 mls of sample, add 0.5 g potassium iodide, and decolourise with dropwise addition of 0.1N sodium thiosulphate to remove any active halogen. Add 0.8 mls 0.02N NaOH solution, and 5 drops indicator. Shake well and compare colour with standards. The closest colour match gives the approximate dimethyl hydantoin concentration.

The results of the three sets of determinations described above are set out in the following Table in which the figures are mg/l of dimethyl hydantoin.

| Sample | HPLC | Procedure (a) | Procedure (b) |
|---|---|---|---|
| A | 50 | 85 | 50 |
| B | 241 | 280 | 250 |
| C | 38 | 85 | 50 |
| D | 243 | 280 | 250 |
| E | 35 | 56 | 50 |
| F | 105 | 122 | 100 |
| G | 24 | 46 | 50 |
| H | 33 | 155 | 150 |

The deviation of the results for Sample H, procedures (a) and (b), from the HPLC result have not been explained and are regarded as non-typical.

Procedure (b) gave a better correspondence than procedure (a) with the actual concentrations. Both procedures (a) and (b) are regarded as being successful in relation to Samples A-G despite the average positive variance which can be seen as beneficial since it acts to trigger action to reduce the dimethyl hydantoin level before it has reached its advisory maximum level.

In another series of tests of procedure (a) thymol phthalein indicator was used. The results are set out in the following Table together with the corresponding HPLC determinations.

| Sample | HPLC | Procedure (a) |
|--------|------|---------------|
| J | 264 | 300 |
| K | 100 | 80 |
| L | 173 | 170 |
| M | 49 | 50 |
| N | 56 | 100 |
| P | 82 | 80 |
| Q | 109 | 80 |
| R | 37 | 30 |

These results tended to vary more between positive and negative variances but are sufficiently accurate for practical monitoring purposes.

We claim:

1. A process for monitoring the quantity of dimethyl hydantoin in a water having a pH of about 7.4 to about 7.8 comprising contacting a volume of a base of known normality with a volume of the water and determining the quantity of dimethyl hydantoin therein according to the non-stoichiometric relationship $0.2 \times 10^{-4}$ equivalents of base = 3.33 mg of dimethyl hydantoin by a procedure selected from:

(a) adding a sufficient volume of the base to a given volume of the water or adding a sufficient volume of the water to a given volume of the base to attain a pH of 9.3 in the water so as to determine the actual quantity of dimethyl hydantoin in the water, or (b) adding a volume of the base corresponding to a preselected concentration level of dimethyl hydantoin to a given volume of the water and determining the deviation of the pH of the water above or below 9.3 to determine the deviation of the concentration of dimethyl hydantoin respectively below or above that level in the water 2. A process as claimed in claim 1 wherein pH is determined by the use of thymol phthalein.

3. A process as claimed in claim 1 wherein there is added to the water, before the addition of the base, a source of soluble iodine followed by a source of thiosulphate or sulphite ions to inactivate active halogen values.

4. A process as claimed in claim 1 wherein the deviation in pH is determined according to procedure (b) by comparing the water to which the base has been added with a series of standard solutions containing different known concentrations of dimethyl hydantoin to which the same quantity of base has been added or with representations of such standard solutions.

* * * * *